United States Patent [19]

Ohama et al.

[11] Patent Number: 5,436,268
[45] Date of Patent: Jul. 25, 1995

[54] PROCESSES INCLUDING GERM-DESTROYING STEP, GERMICIDAL PRODUCTS AND THEIR PREPARATION METHOD, FUMIGANT AND FUMIGATION METHOD, AS WELL AS GERMICIDAL GAS COMPOSITIONS, THEIR PREPARATION METHOD AND APPARATUS THEREFOR

[75] Inventors: Chiaki Ohama, Yokohama; Keisuke Kato, Chiba, both of Japan

[73] Assignee: The Green Cross Corporation, Japan

[21] Appl. No.: 76,833

[22] Filed: Jun. 15, 1993

Related U.S. Application Data

[62] Division of Ser. No. 721,496, Jul. 8, 1991, abandoned.

[30] Foreign Application Priority Data

| Nov. 9, 1989 | [JP] | Japan | 1-291544 |
| Nov. 9, 1989 | [JP] | Japan | 1-291545 |
| Nov. 9, 1989 | [JP] | Japan | 1-291546 |
| Nov. 9, 1989 | [JP] | Japan | 1-291551 |
| Nov. 9, 1989 | [JP] | Japan | 1-291552 |
| Nov. 9, 1989 | [JP] | Japan | 1-291557 |
| Dec. 14, 1989 | [JP] | Japan | 1-325655 |
| Dec. 20, 1989 | [JP] | Japan | 1-330251 |
| Jan. 23, 1990 | [JP] | Japan | 2-014466 |
| Jan. 23, 1990 | [JP] | Japan | 2-014659 |

[51] Int. Cl.$^6$ .............................. A01N 47/46
[52] U.S. Cl. ................................ 514/514
[58] Field of Search ............... 558/17, 18; 514/514; 424/40

[56] References Cited

U.S. PATENT DOCUMENTS

| 3,658,304 | 4/1972 | Hall, Jr. et al. | 261/23 R |
| 3,996,386 | 12/1976 | Malkki et al. | 426/321 |
| 4,067,896 | 1/1978 | Pierce | 260/454 |
| 4,216,217 | 8/1980 | Van der Aa et al. | 424/263 |
| 4,228,165 | 10/1980 | Ogata et al. | 424/248.5 |
| 4,780,279 | 10/1988 | Enos | 422/32 |

*Primary Examiner*—José G. Dees
*Assistant Examiner*—Samuel Barts
*Attorney, Agent, or Firm*—Lorusso & Loud

[57] ABSTRACT

Disclosed are processes for germ-destroying air, water and food, including a germ-destroying step using an isothiocyanic acid ester, germicidal fibers and plastic products and processes for preparing the germicidal fibers and plastic products, fumigants and fumigating processes, as well as germicidal gas composition containing an isothiocyanic acid ester, a process for the preparation thereof and an apparatus for use with the process therefor.

12 Claims, 8 Drawing Sheets

PROCESSES INCLUDING GERM-DESTROYING STEP, GERMICIDAL PRODUCTS AND THEIR PREPARATION METHOD, FUMIGANT AND FUMIGATION METHOD, AS WELL AS GERMICIDAL GAS COMPOSITIONS, THEIR PREPARATION METHOD AND APPARATUS THEREFOR

This application is a division of application Ser. No. 07/721,492, filed Jul. 8, 1991, abandoned.

TECHNICAL FIELD

The present invention relates to processes including germ-destroying step using an isothiocyanate, germicidal products generating a vapor of the isothiocyanate and a method for the germicidal products, fumigants and the method for fumigation, as well as germicidal gas compositions, a method for the preparation of the germicidal gas compositions and an apparatus for use with the method for the preparation thereof.

BACKGROUND OF THE ART

Various foods, glass products such as lenses, leather products such as leather boots, leather jumpers and fur coats and products of paints and pastes formed of starch or cellulose are apt to mold. This considerably reduces validity of the goods or calls for waste disposal thereof.

Apart from mold, increased growth of harmful microorganisms, too, considerably reduces validity of the goods or demands for waste disposal thereof. For example, in the case of foods, there are caused problems of fermentation and food poisoning due to increased growth of bacteria.

It is known to seal-pack an article together with an oxygen absorber with a packing material and to maintain the oxygen concentration within the pack below 1 or less for the purpose of preventing the article from molding. While this method can effectively prevent generation of mold by aerobic bacteria, this cannot be an effective means for preventing increase and growth of anaerobic bacteria which account for food poisoning or fermentation.

It is also known to seal-pack an article together with an ethanol-emanating agent and to fill the inside of the pack with ethanol vapors for the purpose of preventing the formation of mold and the growth of ordinary bacteria. With this method, satisfactory effect cannot be obtained unless ethanol which is expensive is used in a relatively large amount.

Further, a number of mildew-proofing agents and anti-bacterial agents are hitherto known. Most of these chemicals, however, have toxicity to human bodies so that the use thereof is subjected to severe restriction.

A number of natural products having an antimicrobial action are hitherto known. Especially, *Eutrema wasabi* is known to have an excellent germicidal activity. It is also known to subject food to a germ-destroying treatment using an isothiocyanate (hereinafter referred to simply as ISOTC) which is a major component of wasabi. For example, Japanese Published Unexamined Patent Application No. Sho-57-99182 discloses an aqueous emulsion composition obtained by emulsion-dispersing, in water in the presence of an emulsifier, a solution of ISOTC dissolved in an oil. This aqueous emulsion composition is used by mixing into a food so as to sterilizing the food. However, the incorporation of such an aqueous emulsion into foods is not preferable not only because taste of the foods deteriorates but also because ISOTC in foods is apt to decompose. Japanese Published Unexamined Patent Application No. Sho-58-63348 discloses a method for preserving vegetables and fruits wherein the vegetables and fruits are packed in a packaging vessel together with a synthetic zeolite which has a pore diameter of 5–10Å and which is impregnated with ISOTC in a proportion of about 5% by weight. The ISOTC-impregnated zeolite does not emanate an effective amount of ISOTC vapors in air. It can adsorb moisture in air when subjected to a high humidity condition of a relative humidity of 90% or more with the simultaneous generation of ISOTC adsorbed therein. This known method has problems because the synthetic zeolite with a pore diameter of 5–10Å to be used as an absorbent of ISOTC is expensive and because the amount of ISOTC adsorbed thereto is very low of about 5% by weight. The known, ISOTC-absorbed, synthetic zeolite has also a drawback because it cannot emanate ISOTC vapors unless it is subjected to a high humidity condition. Thus, the ISOTC-adsorbed, synthetic zeolite is not effectively utilized as a general ISOTC vapor-generating agent.

As described in the foregoing, several techniques for destroying germs with the use of ISOTC which is a major ingredient of wasabi are known. However, none of them are satisfactory from the practical standpoint.

With attention paid to the fact that the ISOTC as one of major ingredients for wasabi is an oily substance, the present inventors have succeeded in dissolving the ISOTC in a particular oily substance and providing a germicidal composition in a liquid form having an irritating odor controlled to an extremely low level and easy to handle by controlling the concentration of the ISOTC in the liquid form.

The present inventors have previously provided a germicidal composition in a solid form capable of generating the ISOTC vapor by having such an oily germicidal agent contained in a variety of solid materials.

Further, the present inventors have succeeded in providing various germicidal products by having the germicidal composition contained in the various products.

Furthermore, the present inventors have provided methods or processes for gem-destroying articles with the ISOTC vapor and apparatuses to be employed therefor.

Therefore, the present invention has the major object to improve and enlarge the technology for the gem-destroying treatment using the ISOTC.

The present invention has another object to provide a process for preparing germ-free air.

The present invention has a further object to provide a process for preparing germ-free water.

The present invention has a still further object to provide a process for processing food, which contains the gem-destroying treatment.

The present invention has a still further object to provide a process for boiling cereals thereby producing germ-free food products.

The present invention has still further objects to provide a fumigant and a process for fumigation.

The present invention has still further objects to provide various products having germicidal action and a process for producing the same.

The present invention has another still further objects to provide germicidal gas compositions, a process for preparing the germicidal gas compositions, and an apparatus for use with the process therefor.

As a result of extensive research and studies with the attempt to achieve the aforesaid objects, it has been found that the germ-free air can be prepared by admixing the air with the ISOTC vapor to thereby destroy or kill harmful microorganisms contained in the air and removing the ISOTC from the air.

It is also found that the gem-free water can be prepared by admixing the water with the ISOTC vapor to thereby destroy or kill harmful microorganisms contained in the water and removing the ISOTC from the water.

It is further found that the germ-free, processed food can be prepared by processing food in contact with the ISOTC.

It is further found that the germ-free, heat-treated cereals can be prepared by destroying germs on the cereals in contact with the ISOTC and boiling them.

It is still further found that an odor originating from the ISOTC can be removed by admixing the ISOTC vapor with a fragrant ingredient, in bringing the food into contact with the ISOTC vapor.

It is still further found that allyl isothiocyanate among the ISOTC can demonstrate excellent fumigating action.

It is still further found that germicidal products can be prepared by bringing various products or articles into contact with gases containing the ISOTC vapor.

It is still further found that the germicidal gas composition can be prepared by bubbling gases into a mixture of a liquid of the ISOTC or a solution thereof with an organic liquid.

DISCLOSURE OF THE INVENTION

In an aspect, the present invention consists of a process for preparing the germ-free air by admixing the air with the ISOTC vapor to thereby destroy or kill harmful microorganisms contained in the air and removing the ISOTC from the air.

In another aspect, the present invention consists of a process for preparing the germ-free water by admixing the water with the ISOTC to thereby destroy or kill harmful microorganisms contained in the water and removing the ISOTC from the water.

In a further aspect, the present invention consists of a process for preparing the germ-free, processed food by processing food in contact with the ISOTC.

In a still further aspect, the present invention consists of a process for preparing the germ-free, heat-treated cereals by destroying germs on the cereals in contact with the ISOTC and boiling them.

In a still further aspect, the present invention consists of a process for removing an odor originating from the ISOTC so as to fail to be substantially felt or perceived any more by admixing the ISOTC vapor with a fragrant ingredient, in bringing the food into contact with the ISOTC vapor.

In a still further aspect, the present invention consists of a fumigant and a process for providing excellent fumigation action of allyl isothiocyanate.

In a still further aspect, the present invention consists of ISOTC-impregnated germicidal products and a process for producing the products.

In a still further aspect, the present invention consists of a process and an apparatus for preparing the germicidal gas composition by bubbling gases into a mixture of a liquid of the ISOTC or a solution thereof with an organic liquid, and the germicidal gas composition obtained thereby.

The term "germ-destroying action" used in this specification is intended to refer to "antimicrobial action" which includes both germicidal action and germistatic action. The term "gem" herein is intended to involve bacteria, fungi, spore, alga and other harmful microorganisms.

As the isothiocyanate (ISOTC), there may be used various aliphatic and aromatic esters of isothiocyanic acid. Preferably, allyl isothiocyanate ($CH_2=CHCH_2NCS$) and alkyl isothiocyanate (RNCS, R: alkyl) are used. In the present invention, mustard oil may be used as such.

Further, the agent for generating the ISOTC vapor referred in this specification is intended to mean any agent in the form of a liquid, solid or gel, capable of generating the ISOTC vapor from its surface.

Agent for Generating ISOTC Vapor In a Liquid Form

The liquid agent for generating the ISOTC vapor is a solution obtained by dissolving ISOTC in an oily liquid. As the oily liquid, there is used one which has vapor pressure (saturated vapor pressure) at 30° C. of 2 mmHg or less, preferably 1 mmHg or less. Since a solution of ISOTC dissolved in an oily liquid having such a low vapor pressure can significantly suppress the vaporization of ISOTC and since vapors emanating from such a solution contains almost no vapors of the oily liquid and substantially consist of the ISOTC vapors, the contact of an article with such vapors does not cause troubles resulting from the vapors of the oily liquid. An oily liquid having a boiling point of at least 180° C., preferably at least 200° C., more preferably 220° C., is generally advantageously used. As the oily liquid, there may be mentioned, for example, fats and oils such as olive oil, sesame oil, safflower oil, soybean oil, tsubaki oil, corn oil, rape oil, castor oil, sunflower oil, cottonseed oil, peanut oil, cacao butter, palm oil, clove oil, coconut oil, beef tallow, fish oil, hardened oil, turtle oil and yolk oil; waxes such as liquid lanolin; hydrocarbon oils such as liquid paraffin, liquid polyisobutylene and squalane; higher fatty acid oils such as oleic acid, linolic acid and ricinoleic acid; higher alcohols such as octyl alcohol and oleil alcohol; polyalcohols such as polyethylene glycol, polypropylene glycol and glycerin; and ester oils such as linolic acetate and hexyl laurate. It is preferred that the oily liquid be preferably odorless or almost odorless.

The amount of ISOTC dissolved in the oily liquid is 0.01–50% by weight, preferably 0.1–40% by weight based on the oily liquid solution of ISOTC.

The ISOTC generates a strong irritating odor even if present in a small amount and is difficult to handle. However, when used in the form of an oily liquid solution as described above, vaporization of ISOTC is effectively prevented so that ISOTC can be handled without difficulty.

In dissolving ISOTC in the oily liquid, various auxiliary components may be added or dissolved thereinto as desired. Examples of such auxiliary components include a surfactant; a high molecular weight substance; a higher alcohol, a higher fatty acid, a fatty acid ester or a fat oil which are solids at ambient temperature; a colorant; viscosity-controlling agent; and an antioxidant. Further, a lower alcohol such as ethanol or propyl alcohol or a low boiling point solvent such as acetone, methyl ethyl ketone, ether, ethyl acetate or hexane may be added in a small amount as an auxiliary component to control the amount of ISOTC vaporized from the oily liquid.

The ISOTC-containing oily liquid according to the present invention may be prepared by dispersing ISOTC-containing seeds or cells, as such or after pulverization, into an oily liquid. The amount of the seeds or cells dispersed in the oily liquid is 1–80% by weight, preferably 10–60% by weight based on the oily liquid. Such an ISOTC-containing oily liquid may be used under a condition where the seeds or cells are present.

Agent for Generating ISOTC Vapor In a Solid or Gel Form

The agent in a solid form for generating the ISOTC vapor may be obtained by impregnating a porous substance with the above-mentioned oily liquid solution of ISOTC (hereinafter referred to also merely as ISOTC solution). When the porous substance is impregnated with ISOTC by itself, a large amount of ISOTC vapors is generated at the time of impregnation of the porous substance with ISOTC because of the high evaporation rate thereof. As a result, the working environment becomes poor due to ISOTC vapors. Additionally, it becomes difficult for the porous substance to stably support ISOTC for a long period of time since vaporizability of ISOTC carried by the porous substance is still high. According to the present invention, such difficulties can been overcome by supporting ISOTC as a solution dissolved in the above oily liquid to a porous substance by impregnation. While ISOTC easily reacts with water and is poor in storage stability, this problem can been also solved by using it in the form of a solution in the above-mentioned oily liquid.

As the porous substance, those which are generally used as an absorbent, a filler, etc. may be used. Examples of such substances include clay or clay minerals such as diatomaceous earth, yellow earth, clay, talc, zeolite, attapulgite and sepiolite and other substances such as activated carbon, silica, silica gel, alumina, magnesia, silica-alumina, silica-magnesia and synthetic aluminosilicate. As the porous substance, there may be used those of a variety of shapes such as in the form of powder, pellet, sphere, column and cylinder. As the porous substances, it is preferable to use calcined or dried materials from which moisture has been sufficiently removed.

Impregnation of the porous substance with the solution may be performed by a method wherein the porous substance is mixed with the ISOTC solution, a method wherein the ISOTC solution is sprayed over the porous substance, a method wherein the porous substance is immersed in the ISOTC solution, or the like method. The proportion of the ISOTC solution supported by impregnation to the porous substance in not greater than the saturated absorbing capacity of the porous substance and, generally, 1–100 parts by weight per 100 parts by weight of the porous substance. Preferred content is suitably determined according to the kind of the ISOTC solution and the kind of the porous substance.

In the present invention, when the porous substance impregnated with the ISOTC solution is in the form of powder, it is possible to shape it by a conventional shaping method into tablet, spheres, columns, pellets, etc. The shaping may be effected by a tablet shaping method, an extrusion molding method, etc. In performing the shaping, a molding aid is used. Examples of the molding aid include organic binders such as carboxymethyl cellulose, polyvinyl alcohol and sodium alginate and inorganic binders such as bentonire, kaolin, alumina hydrogel and silicic acid hydrogel. As the molding aid, various short fibers such as gypsum whisker may also be used. For the purpose of controlling the emanation of ISOTC, the ISOTC solution-containing porous substance may be coated with a resin capable of allowing the ISOTC vapor to pass therethrough. The provision of such a coating can further suppress the emanation of the ISOTC from the porous substance.

Another type of the agents in a solid form for generating the ISOTC vapor may be obtained by encapsulating the above-mentioned ISOTC solution. The encapsulation may be performed by various known methods, for example, a method wherein the ISOTC solution and a high molecular weight solution are simultaneously ejected into an aqueous medium through inner and outer nozzles, respectively, of a dual liquid nozzle, a surface polymerization method, etc. The encapsulation may also be effected by a method wherein the ISOTC or a porous substance impregnated with the ISOTC solution is mixed with a melt of a fusible material which is solid at room temperature and which has a melting point of 100° C. or less, preferably in the range of 40°–60° C., the resulting mixture being cooled for solidification and then ground. In this case, as the fusible material, there may be mentioned higher alcohols or esters thereof, fats and oils, waxes, etc. The encapsulation may also be effected by a method wherein the ISOTC or a porous substance impregnated with the ISOTC solution is mixed with a melt of a thermosetting resin composition (such as epoxy resin composition or unsaturated polyether resin composition) which is liquid at room temperature or at a temperature of 100° C. or less, the resulting mixture being cooled for solidification and then ground. A reaction of the ISOTC solution with an inclusion compound-forming agent such as cyclodextrin, urea, etc. may also give encapsulated materials.

The above-mentioned ISOTC solution, the porous substance impregnated with the ISOTC solution, the shaped article of the ISOTC solution-containing porous substance and the encapsulated material of the ISOTC solution may be used in a state seal-packed with a packing material. As the packing material, there may be used one at least a portion of which is pervious to ISOTC vapors. Illustrative of such packing materials are films, sheets and vessels pervious to ISOTC vapors and formed of a plastic such as polypropylene, polyethylene or polyethylene/vinyl acetate copolymer. A packing material formed of a plastic impervious to ISOTC vapors may be used as a packing material pervious to ISOTC vapors by forming fine holes using, for example, a laser beam. In addition, paper, non-woven fabric, a surface-treated material of paper or non-woven fabric, or a laminate of a paper, non-woven fabric or cloth with a plastic film pervious to ISOTC vapors may also be used.

The agents in a gel form for generating the ISOTC vapor to be used for the present invention may be obtained by incorporating the above-mentioned ISOTC solution in a gel-like substance.

Various kinds of conventionally known gel-like substances may be used. Illustrative of these substances are agar, carrageenan, gelatin, carboxymethyl cellulose, starch, alginic acid, polyvinyl alcohol and dextrin. The incorporation of the ISOTC solution into the gel-like substance may be effected by a method in which the ISOTC solution is mixed and dispersed in a previously formed gel-like substance, a method in which the ISOTC solution is added during the preparation of the gel-like substance, especially to a raw material for the preparation of the gel-like substance, or the like method. The content of the ISOTC in the gel-like substance is generally 0.05–20% by weight, preferably 0.5–10% by weight. A concrete content of ISOTC is adequately determined according to the object of use of the gel-like substance. In case where the ISOTC solution is incorporated into the gel-like substance, the ISOTC solution may be used as a previously encapsulated form.

The above-mentioned ISOTC vapor-generating agent in the gel form to be used for the present invention is generally used after being filled or packed in a bag of a paper which has been subjected to a water-repelling or oil-repelling treatment or in a bag or vessel formed of a plastic. As a bag of a plastic film or vessel, there is used one which is pervious to ISOTC vapors.

The present invention will be described in more detail hereinafter.

(1) Process for Preparing Germ-Free Air

Figure 1:
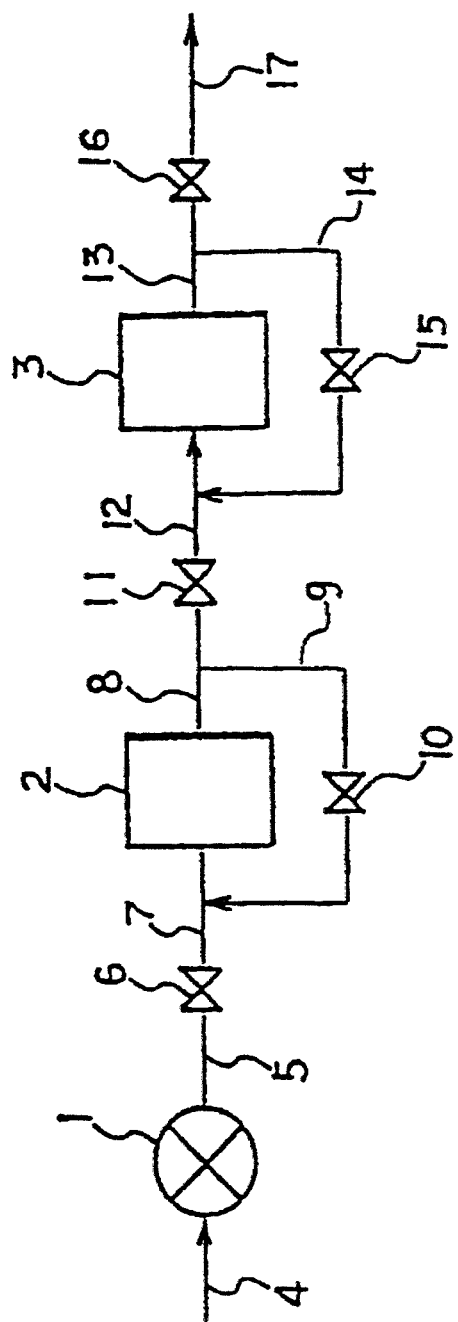
FIG. 1 is a flow sheet for a process for preparing germ-free air.

In accordance with the present invention, germ-free air may be prepared in accordance with the flow sheet as shown in FIG. 1.

As shown in FIG. 1, reference numeral 1 denotes a blower, reference numeral 2 denotes an ISOTC vapor-generating chamber, reference numeral 3 denotes an adsorbing device, the ISOTC vapor generating chamber 2 is provided with a heating mechanism or a cooling mechanism, each of which is filled with an ISOTC-generating agent.

The ISOTC adsorbing device 3 contains an adsorbing agent within its inside and vapor of the ISOTC contained in the air introduced therein is removed from the air by adsorption. The adsorbing agent may generally include, for example, activated carbon, sepiolite, alumina, silica-alumina and so on, although any agent may be employed as long as it can adsorb the vapor of the ISOTC.

In preparing the gem-free air, a blower 1 is operated to supply air to the vapor-generating chamber 2 through a line 4 while discharging the air containing the vapor of the ISOTC through a line 8, thereby introducing this air to the adsorbing device 3 in which the ISOTC contained in the air is adsorbed on the adsorbing agent and removed from the air and discharging the air containing no ISOTC through lines 13 and 17.

In accordance with the present invention, the air discharged from the adsorbing device 3 reduces the number of microorganisms to such a remarkably decreased level as being substantially free from microorganisms. In other words, the vapor of the ISOTC is admixed with the air in the vapor-generating chamber 2, thereby destroying microorganisms contained in air. In this case, the concentration of the vapor of the ISOTC to be admixed with the air may range from 10 ppm to 4,000 ppm (v/v), preferably from 50 ppm to 1,000 ppm (v/v), on the volume basis. The contact period of time between the ISOTC and the air may range as short as from 1 second to 120 seconds and may be adjusted by recirculating a portion of the air to be discharged through the line 8 from the vapor-generating chamber 2 through the line 9 and the valve 10 to the line 7. By bringing the ISOTC into contact with the air, the microorganisms contained in the air is destroyed or combated.

It is to be noted that the air discharged from the adsorbing device 3 does not substantially contain any vapor of the ISOTC. In other words, the adsorbing device 3 adsorbs the vapor of the ISOTC by the aid of the adsorbing agent contained therein and removes it from the air. The contact period of time between the water and the ISOTC in the adsorbing device may be as long as required for removal of the ISOTC by adsorption and be adjusted by recirculating a portion of the air to be discharged through the line 13 from the adsorbing device 3 through a line 14 and a valve 15 to the line 12. The adsorbing device 3 may be provided with a heating mechanism or a cooling mechanism to thereby control the temperature at which the ISOTC is adsorbed. When the adsorbing agent contained in the adsorbing device has adsorbed the ISOTC to a saturated level, the adsorbing agent can be recovered by passing a heating medium such as steam through it.

In accordance with the present invention, it can be noted that the introduction of the ISOTC may be carried out by spraying an ISOTC liquid or a solution thereof directly into air and gasifying it in the air, in addition to the admixture of the gasified ISOTC with the air in the vapor-generating chamber. In this case, a mist separator may be disposed on the downstream side from the portion at which the ISOTC is sprayed, thereby separating and removing non-gasified ISOTC in a form of liquid drops from the air. Further, it can be noted that the ISOTC can be removed from the air in a chemically reactive manner, not by the aid of the adsorbing agent, by using a substance having reactivity with the ISOTC, such as a solid amine or the like.

The method in accordance with the present invention can produce germ-free air at cheap costs and with high efficiency. It is further to be noted that, even if a very minute amount of the ISOTC would be left in the resulting germ-free air, such a germ-free air is not hazardous at all to the human body.

(2) Process for Preparing Germ-Free Water

Figure 2:
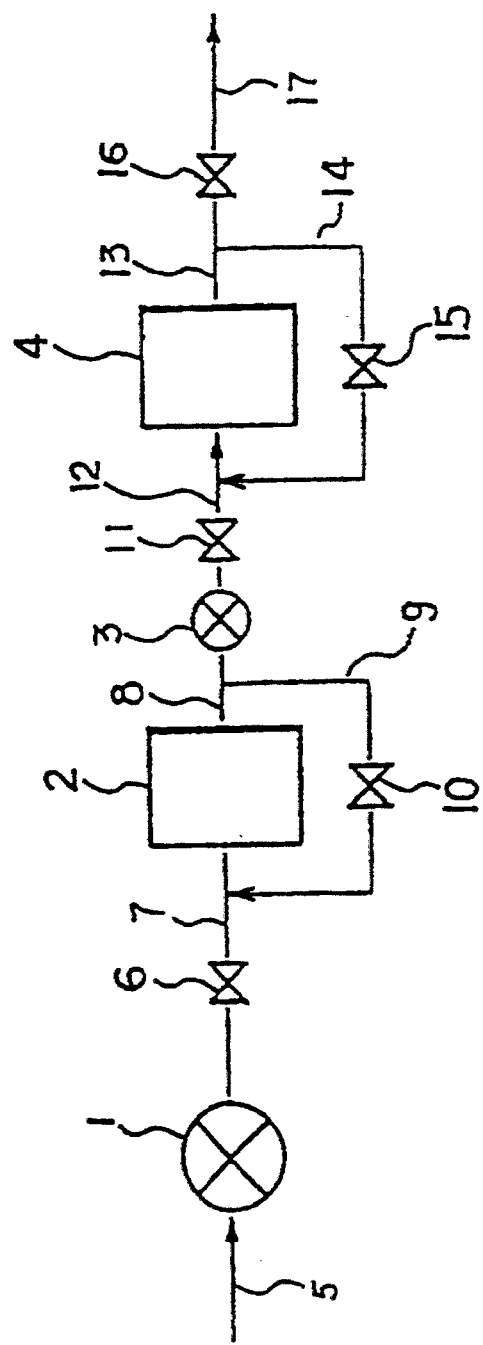
FIG. 2 is a flow sheet for a process for preparing germ-free water.

In accordance with the present invention, germ-free water may be prepared in accordance with the flow sheet as shown in FIG. 2, in which reference numeral 1 denotes a pump, 2 denotes a gem-destroying vessel, and 4 denotes an adsorbing device.

The gem-destroying vessel 2 may be of any shape, such as a container, a tank or the like, and is not restricted to a particular shape as long as it can be used for mixing the ISOTC with water. As the method of mixing the ISOTC with water, there may be enumerated, for example, a method for introducing vapors of the ISOTC into water, a method for admixing an ISOTC liquid or a solution thereof with water, and a method for placing a solid material so immobilized as to contain the ISOTC therein in water and allowing the ISOTC to be gradually released from the solid material.

As methods for immobilizing the ISOTC on the solid material, there may be mentioned, for example, a method for impregnating a porous material in such a form of powder, pellet or plate with the ISOTC liquid or a solution thereof, a method of molding or impregnating powders of the porous material with the ISOTC liquid or the solution thereof and molding or forming the resulting porous material powders into pellets or plates with the aid of a polymer binder, and a method of coating a resin onto surfaces of the porous material impregnated with the ISOTC liquid or the solution thereof. The rate of the ISOTC with which the porous material is to be impregnated may range from approximately 1% to 25% by weight. The porous material may include, for example, active carbon, silica, alumina, silica-alumina, magnesia, sepiolite, diatomaceous earth, zeolite, and so on.

The ISOTC-adsorbing device 4 contains an adsorbing agent in its inside and is so arranged as to adsorb the ISOTC and remove it from the water introduced thereinto. The adsorbing agent may include, for example, activated carbon, sepiolite, alumina, silica, silica-alumina, magnesia, diatomaceous earth, zeolite and any other agent that can demonstrate an adsorbing action for the ISOTC.

In germ-destroying water, the pump 1 is first operated to introduce water through a line 5 into the sterilizing vessel 2 into which the ISOTC in turn is admixed. Then, the water containing the ISOTC is discharged from the germ-destroying vessel 2 through a line 8 by operating a pump 3, thereby introducing the water into the adsorbing device 4 which in turn adsorbs the ISOTC contained in the water and remove it from the water, followed by discharging the water containing no ISOTC through a line 13 and then a line 17.

In accordance with the present invention, the water discharged from the adsorbing device 4 is free from microorganisms. In other words, the microorganisms contained in water can be destroyed or combated in the germ-destroying vessel 2 by admixing water with the ISOTC. In this case, the concentration of the ISOTC may range from 10 ppm to 5,000 ppm, preferably from 50 ppm to 2,000 ppm, on the weight basis. The contact period of time between the ISOTC and the water may range as short as from 1 second to 120 seconds, and it can be adjusted by circulating a portion of the water discharged from the germ-destroying vessel 2 through lines 9 and a valve 10 to the line 7. This contact treatment of water with the ISOTC can destroy or combat microorganisms contained in water.

The water discharged from the adsorbing device 4 does not contain any substantially amount of the ISOTC. In other words, the adsorbing device 4 allows the adsorbing agent contained therein to adsorb the ISOTC thereon and remove it from the water. The contact period of time between the water and the ISOTC may be as long as required for removal of the ISOTC by adsorption and be adjusted by recirculating a portion of the water to be discharged through the line 13 from the adsorbing device 3 through a line 14 and a valve 15 to the line 12. The adsorbing device 4 may be provided with a heating mechanism or a cooling mechanism to thereby control the temperature at which the ISOTC is adsorbed. When the adsorbing agent contained in the adsorbing device has adsorbed the ISOTC to a saturated level, the adsorbing agent can be recovered by passing a heating medium such as steam through it.

In accordance with the present invention, it can be noted that the ISOTC may be introduced directly into water passing through a piping and through the germ-destroying vessel as well. Further, it can be noted that the ISOTC can be removed from the water in a chemically reactive manner by using a substance having reactivity with the ISOTC, such as a solid amine or the like.

(3) Process for Processing Food

Figure 3:
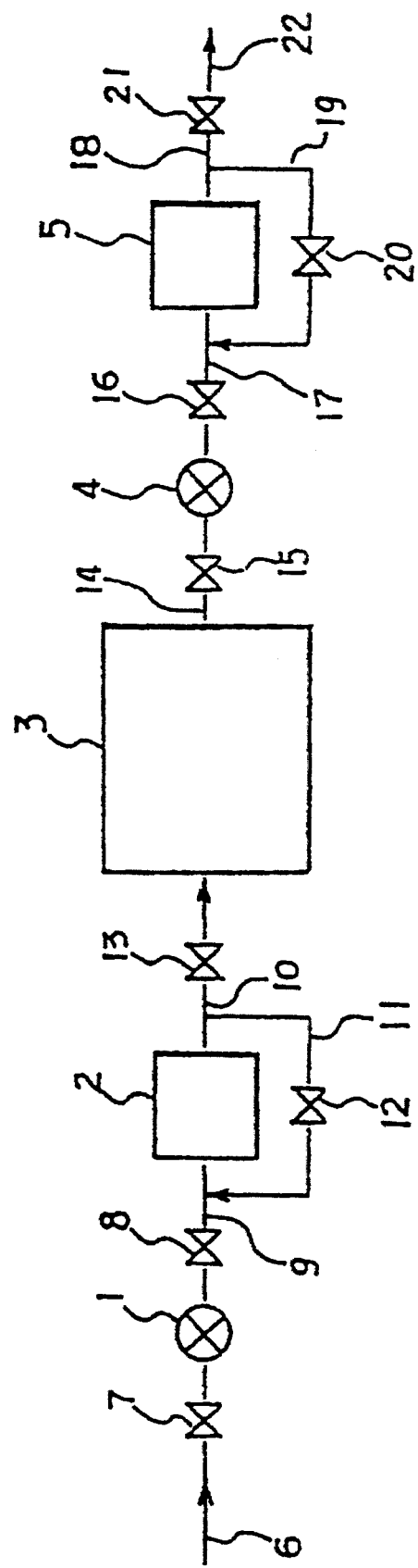
FIG. 3 is a flow sheet for a process for bringing a material to be treated into contact with the ISOTC vapor.

In accordance with the present invention, food may be processed in accordance with the flow sheet as shown in FIG. 3, in which reference numerals 1 and 4 denote blowers, reference numeral 2 denotes an ISOTC vapor-generating chamber, reference numeral 3 denotes a processing device, and reference numeral 5 denotes an ISOTC adsorbing chamber.

The ISOTC vapor generating chamber 2 may be of any shape that can contain an ISOTC vapor generating agent within the inside thereof.

The ISOTC adsorbing device 5 contains an adsorbing agent in its inside and is so arranged as to adsorb the ISOTC vapor and remove it from the gas introduced thereinto.

In processing food, the blower 1 is first operated to introduce gas through a line 6 into the ISOTC vapor-generating chamber 2 into which the ISOTC in turn is admixed. Then, the gas containing the ISOTC vapor is discharged from the ISOTC gas generating chamber 2 through a line 10 by operating a pump 3, thereby introducing the gas into the food processing device 3 which in turn is filled with the raw food to be processed. As the gas for carrying the ISOTC vapor, there may usually be employed air, although nitrogen gas or carbon gas may be employed. A portion of the gas to be discharged from the ISOTC vapor-generating chamber 2 is recirculated through the line 11 and the valve 12 to the line 9, thereby adjusting the concentration of the ISOTC in the gas passing through the line 10.

The concentration of the ISOTC vapor in the processing atmosphere within the processing device 3 may range from 10 ppm to 4,000 ppm (v/v), preferably from 200 ppm to 2,000 ppm (v/v), on the weight basis.

The gas containing the ISOTC vapor introduced into the processing device 3 is brought into contact with the raw food to be processed herein, thereby carrying out germ-destroying treatment. The gas within the processing device is discharged from the line 22 through the blower 4 and the adsorbing device 5 into the outside. A portion of the gas discharged from the processing device 3 through the line 14 is recirculated through a flow valve into the processing device. The adsorbing device 5 allows the adsorbing agent contained therein to adsorb the ISOTC vapor thereon and remove it from the gas. The contact period of time between the gas and the ISOTC vapor in the adsorbing device may be as long as required for removal of the ISOTC by adsorption and be adjusted by recirculating a portion of the water to be discharged through the line 18 from the adsorbing device 5 through a line 19 and a valve 20 to the line 17. The adsorbing device 5 may be provided with a heating mechanism or a cooling mechanism to thereby control the temperature at which the ISOTC is adsorbed. When the adsorbing agent contained in the adsorbing device has adsorbed the ISOTC to a saturated level, the adsorbing agent can be recovered by passing a heating medium such as steam through it.

In accordance with the present invention, it can be noted that the introduction of the ISOTC may be carried out by spraying an ISOTC liquid or a solution thereof directly into the atmosphere within the processing device 3 and gasifying it into the gas, in addition to the admixture of the gasified ISOTC with the air in the vapor-generating chamber 2. Further, it can be noted that the ISOTC can be removed from the gas in a chemically reactive manner, not by the aid of the adsorbing agent, by using a substance having reactivity with the ISOTC, such as a solid amine or the like.

In accordance with the present invention, it is further to be noted that the gas containing the ISOTC is not necessarily allowed to pass through the processing device in a continuous manner. Once the gas is introduced into the processing device, the valve 13 is closed to thereby process the food within the processing device, and after completion of the processing of the food, the valve 15 is opened to thereby discharge the gas containing the ISOTC from the processing device.

The processing device 3 may be of any shape as long as it can be of a closed structure. Many conventional food processing devices are of a closed structure, so that they may be employed for the present invention by providing a gas inlet and a gas outlet on a peripheral closed wall of the device. A processing device of an open structure may also be employed by providing a closed housing or chamber and providing a gas inlet and a gas outlet on a peripheral wall of the housing or the chamber. The processing device may be of a batch type or of a continuous type.

It is to be noted that a closed structure of the processing device to be used for the present invention may not necessarily be full and the processing device may be of such a structure as a small amount of the ISOTC may leak as long as the working circumstance would not be worsened due to its irritating odor because the ISOTC is very high in safety against the human body.

The present invention may be applied to the processing under wet conditions such as grinding processing in water. In this case, it is such that the ISOTC may be added to the water.

The preferred specific embodiments for the processing of the food in accordance with the present invention may include, for example, pulverizing (forming into flour), peeling, pressurizing, smashing, pressing, cutting, mixing, kneading, filtering, centrifugal separating, sieving (into grains), rolling, molding, cooling, heating at low temperatures, cooking, boiling, drying and so on.

The specific embodiments of the processing processes may be mentioned in terms of raw food material as follows:

(a) mechanical processing, such as polishing, pulverizing or sieving, of cereals, e.g., rice, wheat, buck wheat, corn and so on;

(b) mechanical processing, such as smashing, pulverizing or sieving, of "konyaku" potatoes, sweet potatoes, potatoes, tapioca and other potatoes;

(c) a series of processing for preparing noodle from wheat flour;

(d) aging of meats;

(e) a series of processing for preparing fish paste from fish meat;

(f) processing such as slicing, mashing or grinding raw meat;

(g) drying processing of cut fish or cooked food; and (h) drying processing of fruit.

In food processing method according to the present invention, the raw food to be processed has its storage performance improved to a considerably high degree, as compared with the food processed according to conventional processing method, because it is subjected to germ-destroying action due to the ISOTC as well as it is processed. The ISOTC to be used for the present invention is so highly safe against the human body that the processed food resulting to the process according to the present invention does not adversely affect the human body at all even if the ISOTC would be left in a very small amount within the processed food.

(4) Process for Treating or Cooking Cereals

In accordance with the present invention, cereals may be treated or cooked in accordance with a flow sheet as shown in FIG. 3. In this case, a treating chamber 3 is employed in place of the processing device 3.

In heat-treating the cereals with the ISOTC vapor, the blower 1 is first operated to introduce gas through a line 6 into the ISOTC vapor-generating chamber 2 into which the ISOTC in turn is admixed. Then, the gas containing the ISOTC vapor is discharged from the ISOTC gas generating chamber 2 through a line 10, thereby introducing the gas into the treating chamber 3 which in turn is filled with the raw food to be processed. As the gas for carrying the ISOTC vapor, there may usually be employed air, although nitrogen gas or carbon dioxide gas may be employed. A portion of the gas to be discharged from the ISOTC vapor-generating chamber 2 is recirculated through the line 11 and the valve 12 to the line 9, thereby adjusting the concentration of the ISOTC in the gases passing through the line 10.

When the ISOTC vapor is introduced in a given concentration in the gas within the treating chamber 3, the blower 1 is suspended and the valve 13 is closed, thereby retaining the treating chamber in a closed state. By retaining the treating chamber in such a closed state for a given period of time, the cereals placed in the treating chamber are allowed to be treated with the ISOTC. It is preferred that the treating chamber 3 is provided with a fan, thereby allowing the air to flow within the treating chamber 3 and promoting dispersion of the ISOTC vapor. The concentration of the ISOTC vapor in the treating chamber may range from 500 ppm to 2,000 (v/v). The treating period of time may be as long as required for germ-destroying the cereals to a sufficient extent and may vary with the concentration of the ISOTC vapor within the treating chamber so that it cannot be determined uniformly. However, the treating period of time may generally range from 10 minutes to 2 hours.

After the completion of the treatment with the ISOTC vapor, the valve 15 is opened and the blower 4 is operated, thereby discharging the gas within the treating chamber 3 into open air from the line 22 through the adsorbing device 5. In this case, the treating chamber 3 is provided with a valve separately from the valve 15, thereby opening this valve so as to allow the gas within the chamber to be released into the open air, in order to avoid the reduction in the pressure within the treating chamber 3. The adsorbing device 5 allows the adsorbing agent contained therein to adsorb the ISOTC vapor thereon and remove it from the gas. The contact period of time between the gas and the ISOTC vapor in the adsorbing device may be as long as required for removal of the ISOTC by adsorption and be adjusted by recirculating a portion of the water to be discharged through the line 1 8 from the adsorbing device 5 through a line 19 and a valve 20 to the line 17. The treating chamber 3 or adsorbing device 5 may be provided with a heating mechanism or a cooling mechanism to thereby control the temperature at which the ISOTC is adsorbed.

In accordance with the present invention, it can be noted that the introduction of the ISOTC may be carried out by spraying an ISOTC liquid or a solution thereof directly into the atmosphere with in the treating chamber 3 and gasifying it in to the gas, in addition to the admixture of the gasified ISOTC with the air in the vapor-generating chamber. Further, it can be noted that the ISOTC can be removed from the gas in a chemically reactive manner, not by the aid of the adsorbing agent, by using a substance having reactivity with the ISOTC, such as a solid amine or the like.

The treating chamber 3 may be of any shape as long as it can be of a closed structure. The gas containing the ISOTC vapor may be introduced into the treating chamber 3 continuously or intermittently and withdrawn continuously therefrom through the line 14. In this case, a portion of the gas withdrawn from the line 14 may be recirculated to the treating chamber 3 through a flow valve.

The cereals may be treated within the treating chamber 3 in a continuous system or in a batch system. When the cereals are to be treated in a continuous system, they may be allowed to pass through the treating chamber 3 at a constant speed. In order to shorten the period of time for treatment within the treating chamber, the pressure within the treating chamber containing the cereals is reduced and then the gas containing the ISOTC vapor is to be introduced into the treating chamber 3. Alternatively, the gas containing the ISOTC vapor is introduced into the treating chamber 3 in which the cereals are placed, and then the treating chamber 3 is pressurized.

As a simplified process for treating the cereals with the ISOTC by the process according to the present invention, the cereals are placed in a plastic bag and an ISOTC liquid or a solution containing the ISOTC is sprayed into the bag or an adsorbing agent impregnated with the ISOTC liquid or the solution containing the ISOTC, followed by closing the bag.

It is noted that the cereals treated with the ISOTC are then boiled with water in customary manner.

For the boiled cereals prepared by the process in accordance with the present invention, heat resistant germs adhering to the cereals, which are not killed at temperatures as high as 100 degrees, are killed or destroyed by the ISOTC, so that storage performance of the cereals can be improved to a remarkably high extent. As the ISOTC can be decomposed by heating in the presence of water, the cereals boiled does not generate strong odor any more.

(5) Process for Retaining Freshness of Food and Agent for Retaining Freshness of Food The process for retaining freshness of food according to the present invention involves admixing a fragrant component with the ISOTC vapor for solving the problem on the odor originating from the ISOTC.

When the ISOTC is employed for retaining the degree of freshness of food, it smells unpleasant to consumers even in a very low concentration, so that the unpleasant smell generating from the ISOTC should be suppressed. In particular, for fragrant food containing fragrant components, importance is placed on the fragrance so that it is desired that the odor originating from the ISOTC should be suppressed as much as possible. As a result of extensive research with the attempt to improve this point, it has been found by the present inventors that when a fragrant ingredient is introduced into vapor of the ISOTC, the fragrance generating from the fragrant ingredient can suppress the odor originating from the ISOTC to such an extent that the odor of the ISOTC does not smell any more, thereby advantageously achieving freshness of food by means of the ISOTC.

The material for retaining the degree of freshness of food according to the present invention can generate the ISOTC vapor and odor or fragrance and is so prepared as to allow a base material to contain the ISOTC and the fragrant ingredient.

As the fragrant ingredients, there may be used one which are in a liquid form or a solid form at ambient temperatures and the solid ones may be used in a form in which they are dissolved in a liquid. Specific examples of the fragrant ingredients may include a variety of essential oil and agents for imparting a flavor to food.

The base material may include, for example, paper, non-woven cloth, plastic films, adsorbing agents and so on.

The material useful for retaining freshness of food may be prepared by having the ISOTC and the fragrant ingredient contained in the base material. For instance, when the base material is such capable of absorbing a liquid or adsorbing gases, such as paper, non-woven cloth or adsorbing agents, the material for retaining freshness of food may be prepared by impregnating the base material with a liquid containing the ISOTC and the fragrant ingredient agent or by having mixed vapor generated from the liquid adsorbed thereon. When the base material is such having no capability of absorbing a liquid or adsorbing gases, such as plastic films, the material for retaining the degree of freshness of food may be prepared by first preparing a coating solution containing the ISOTC, the fragrant ingredient, a filler, and a binder resin and then coating the base material with such a coating solution. In this case, the binder resin may preferably be a curable resin which can be cured or set by exposure to heat or ultraviolet rays, although thermoplastic resins, rubbers, natural polymers and so on may be employed. As the fillers, there may be employed, for example, inorganic or organic fine powder such as finely divided silica or zeolite, calcium carbonate, pulp flour and so on.

A liquid containing the fragrant ingredient and the ISOTC to be used as a raw solution for the preparation of the material for retaining freshness of food may be prepared by dissolving the fragrant ingredient and the ISOTC in a substantially odorless organic liquid such as liquid paraffin, polyethylene glycol, polypropylene glycol, glycerin or the like. In this case, the concentration of the ISOTC in the organic liquid may range usually from 0.01% to 30% by weight, preferably from 0.1% to 20% by weight. The concentration of the fragrant ingredient may be set to such a concentration as substantially suppressing to such an extent that the ISOTC does not smell any more and may vary with the kind of the fragrant ingredient, although it may be 1.5 times the weight of the ISOTC or more, preferably in the range from approximately two to twenty times the weight of the ISOTC. The raw solution may also be prepared by dissolving the ISOTC in essential oil constituting the fragrant ingredient or in the organic liquid. In this case, the concentration of the ISOTC in essential oil or in the organic liquid may range usually from 0.1% to 30% by weight, preferably from 1% to 20% by weight.

The method for retaining the degree of freshness of food according to the present invention may be practiced by packing fragrant food, together with the material for retaining the degree of freshness of food, with the packaging material such as a packing container, packing bag, packing box or the like. Such packed food is subjected to germ-destroying treatment as a result of contact with vapor of the ISOTC generating from the material for retaining the degree of freshness of food packed therein, thereby preventing generation of mold or fungi and transformation due to harmful microorganisms. Furthermore, when the packed food is opened, no odor originating from the ISOTC smells any more due to fragrance generated from the fragrant ingredient contained in the material for retaining the degree of freshness of food, thereby causing consumers no unpleasant smell due to the ISOTC employed for retaining the degree of freshness of food. Further, in accordance with the present invention, substantially the same effect achieved by packing food together with the material for retaining freshness of food can be achieved by spraying a liquid or vapor resulting from the liquid containing the fragrant ingredient and the ISOTC in packing food. In order to achieve the preferred germicidal effect by vapor of the ISOTC in the packed food, the concentration of the ISOTC vapor in the pack may be usually 10 ppm or higher, preferably in the range from approximately 50 ppm to 500 ppm, on the volume basis.

The present invention can preferably be applied to the fragrant food which places importance particularly upon flavor. It is advantageous that the fragrant ingredient to be employed together with the ISOTC can impart flavor identical to or similar to the fragrant ingredient contained in the food. The selection of such a flavor presents the advantages that the flavor of the food is enriched thereby increasing an added value as products.

(6) Fumigant and Process for Fumigation

Heretofore, methyl bromide has been generally employed as a fumigant, however, it has the drawbacks that it is in a gaseous state at ambient temperature and it is flammable. It is further known to be strongly toxic to the human body. It is also known that methyl isothiocyanate has a fumigating property. Further, it has been found that, among isothiocyanate esters, allyl isothiocyanate (hereinafter referred to as ISOTCA) is highly safe and easy to handle as well as is so strong in fumigating action as to be useful as a fumigant.

The fumigation process in accordance with the present invention may be practiced and will be described in detail with reference to a flow sheet similar to FIG. 3 in which reference numeral 3 denotes a fumigating chamber in which the material to be treated is brought into contact with the ISOTCA or its vapor.

In carrying out fumigation, the blower 1 is first operated to introduce gas through a line 6 into the ISOTCA vapor generating chamber 2 into which the ISOTCA in turn is admixed. Then, the gas containing the ISOTCA vapor is discharged from the ISOTCA gas generating chamber 2 through a line 10, thereby introducing the gas into the fumigating chamber 3. As the gas for carrying the ISOTCA vapor, there may usually be employed air, although nitrogen gas or carbon gas may be employed. A portion of the gas to be discharged from the ISOTCA vapor generating chamber 2 is recirculated through the line and the valve 12 to the line 9, thereby adjusting the concentration of the ISOTCA in the gas passing through the line 10.

When the ISOTCA vapor is introduced in a given concentration in the gas within the fumigating chamber 3, the blower 1 is suspended and the valve 13 is closed, thereby retaining the fumigating chamber in a closed state. By retaining the fumigating chamber in such a closed state for a given period of time, the fumigating material placed in the fumigating chamber are allowed to be fumigated with the ISOTCA. It is preferred that the fumigating chamber 3 is provided with a fan, thereby allowing the air to flow within the fumigating chamber 3 and promoting dispersion of the ISOTCA vapor. The concentration of the ISOTCA vapor in the fumigating chamber may range from 10 ppm to 4,000 (v/v), preferably from 200 ppm to 2,000 ppm (v/v), on the volume basis. The fumigating period of time may be as long as required for germ-destroying the fumigating material to a sufficient extent and may vary with the concentration of the ISOTCA vapor within the fumigating chamber so that it cannot be determined uniformly. However, the fumigating period of time may generally range from six hours to three days. The ISOTCA vapor has high permeability so that it has strong fumigating action. Hence, the use of the ISOTCA can shorten the fumigating period of time as compared with methyl bromide as have been conventionally employed for fumigation.

After the completion of the fumigation with the ISOTCA vapor, the valve 15 is opened and the blower 4 is operated, thereby discharging the gas within the fumigating chamber 3 into open air from the line 22 through the adsorbing device 5. In this case, the fumigating chamber 3 is provided with a valve separately from the valve 15, thereby opening this valve so as to allow the gas within the chamber to be released into the open air, in order to avoid the reduction in the pressure within the fumigating chamber 3. The adsorbing device 5 allows the adsorbing agent contained therein to adsorb the ISOTCA vapor thereon and remove it from the gas. The contact period of time between the gas and the ISOTCA vapor in the adsorbing device may be as long as required for removal of the ISOTCA by adsorption and be adjusted by recirculating a portion of the water to be discharged through the line 18 from the adsorbing device 5 through a line 19 and a valve 20 to the line 17. The adsorbing device 5 may be provided with a heating mechanism or a cooling mechanism to thereby control the temperature at which the ISOTCA is adsorbed. When the adsorbing agent packed in the adsorbing device has reached its saturation level, a heating medium such as steam is passed through the adsorbing agent to thereby recover its adsorbing activity.

In accordance with the present invention, it can be noted that the introduction of the ISOTCA may be carried out by spraying an ISOTCA liquid or a solution thereof directly into the atmosphere within the fumigating chamber 3 and gasifying it into the gas, in addition to the admixture of the gasified ISOTCA with the air in the vapor-generating chamber. Further, it can be noted that the ISOTCA can be removed from the gas in a chemically reactive manner, not by the aid of the adsorbing agent, by using a substance having reactivity with the ISOTCA, such as a solid amine or the like.

A portion or a whole portion of the blower, the vapor generating chamber and/or the adsorbing device may be disposed in the fumigating chamber.

The fumigating chamber 3 may be of any shape as long as it can be of a closed structure and, for example, warehouse or storehouse buildings, ship hatches, closed rooms, tents and so on may be employed as fumigation chamber.

The fumigation treatment in accordance with the present invention may be carried out simply by using plastic containers or bags. In carrying out the fumigation using the plastic containers or bags, the fumigating material is placed in the container or bag and the ISOTCA liquid or a solution thereof is sprayed into the container or bag or an agent capable of evaporating the ISOTCA vapor is placed therein, too, followed by closing the container or bag and allowing it to stand for a given period of time.

The fumigating material may include, for example, cereals and seeds, such as rice, wheat, corn, buck wheat, broad beans, soy beans, adzuki beans, and so on, fruits, vegetables, wood, and other natural crops which the growth or proliferation of harmful microorganisms or insects may cause problems.

In accordance with the present invention, in carrying over cereals by means of air, the cereals may be fumigated with the ISOTCA vapor during conveying them through air by mixing the ISOTCA vapor with the air. When the cereals stored in the warehouses are to be transported, the air is forced into pipings by the blower and the cereals are sucked and conveyed in a suspended state together with the pressurized air. In accordance with the present invention, the ISOTCA vapor may be admixed with a carrying air, thereby achieving the good fumigating effects. As the method for admixing the ISOTCA vapor with the carrying air, there may be mentioned, for example, a method for forcing the ISOTCA vapor into the air passing through the piping, a method for forcing a liquid of the ISOTCA or a solution thereof and gasifying it within the piping, a method for mixing the ISOTCA vapor or liquid into the air coming into the blower, and so on. In carrying over the cereals with the carrying air, the cereals may be so arranged as to be discharged from a top end of the piping located at a given location, together with the air and separating the cereals from the air. The carrying air separated from the cereals contains the ISOTCA vapor which may preferably be recirculated into the blower.

The ISOTCA to be employed for the present invention may also be employed as a soil fumigant. In the agricultural application, harmful microorganisms and insects within the soil are killed or combated, thereby increasing the harvest of crops. The ISOTCA has high germicidal and insecticidal action and strong permeability and dispersibility. Further, it is highly safe against the human body. From these points, the ISOTCA is said to be remarkably good as a soil fumigant. In applying the ISOTCA to the soil, the ISOTCA liquid or a solution thereof in water or in an organic solvent is sprayed to the soil or poured into the soil. Further, it is to be noted that the ISOTCA can be decomposed with water so that even if it is employed in a large amount, it can be decomposed naturally as time elapses. This is extremely advantageous in applying the ISOTCA as the soil fumigant.

The fumigant comprising the ISOTCA in accordance with the present invention is liquid at ambient temperatures and extremely low in flammability and highly safe against the human body, unlike methyl bromide which has conventionally been employed widely as a fumigant. Hence, the ISOTCA has the remarkable advantages even if it would be employed in a very small amount.

By employing the fumigant according to the present invention, the fumigating material which the growth or proliferation of harmful microorganisms or insects may cause the problems can be fumigated with high safety and effectiveness. Further, the fumigant according to the present invention can advantageously be applied as a soil fumigant or soil sterilizer.

(7) Germicidal Products and Process for Preparation of the Same

In accordance with the present invention, the germicidal products are such that they can adsorb the ISOTC on their surfaces and at the same time generate the ISOTC vapor from the surfaces thereof. Such products may be prepared in accordance with a flow sheets as shown in FIG. 3 in which reference numeral 3 denotes a treating chamber.

In preparing the germicidal products (hereinafter referred to sometimes as the material to be treated or as related words), the blower 1 is operated to supply gases to the vapor-generating chamber 2 through a line 6 while discharging the gases containing the vapor of the ISOTC through a line 10, thereby introducing the gases into the treating chamber 3 in which the material to be treated is accommodated. As the gases together with which the vapor of the ISOTC is carried, there may usually be employed air, although nitrogen gas and so on may also be used. The concentration of the ISOTC vapor in the gases to be discharged from the vapor-generating chamber 2 may be adjusted by recirculating a portion of the gases through the line 11 and the valve 12 to the lines 9.

When the vapor of the ISOTC is admixed in the required concentration with the air in the treating chamber 3, the blower 1 is suspended and the valve 13 is closed to retain the treating chamber in a closed state. The ISOTC is allowed to be adsorbed on the material to be treated while the closed state is retained for a predetermined period of time. In the treating chamber 3, a fan is provided to flow the air within the chamber and a dispersion of the vapor of the ISOTC within the chamber is preferably enhanced. The concentration of the ISOTC vapor within the treating chamber may range from 200 ppm to 5,000 ppm (v/v), preferably from 200 ppm to 2,000 ppm (v/v), on the volume basis. The treating period of time may last as long as a sufficient amount of the ISOTC can be adsorbed on the material to be treated and it may vary with the kind of the material to be treated or the concentration of the ISOTC vapor within the treating chamber and cannot be determined in a uniform manner, but it may generally range from 1 minute to 60 minutes, preferably from 5 minutes to 20 minutes. The vapor of the ISOTC to be used for the present invention has a very high degree of permeability and it is adsorbed strongly on the material to be treated.

After the adsorption treatment has been finished, the valve 15 is opened and a blower 4 is so operated as to discharge the air within the treating chamber into the open atmosphere from a line 22 through the adsorbing device 5. In this case, in order to avoid the reduction in the pressure within the treating chamber, a valve may be mounted to the treating chamber so as to release the air into the open air therethrough. The adsorbing device 5 is so filled with the adsorbing agent as to adsorb the ISOTC vapor contained in the air and remove it from the air. The contact period of time between the air and the ISOTC in the adsorbing device may be as long as required for removal of the ISOTC by adsorption to a sufficient extent and be adjusted by recirculating a portion of the air to be discharged through the line 18 from the adsorbing device 5 through a line 19 and a valve 20 to the line 17. The treating chamber 3 and the adsorbing device 5 may be provided with a heating mechanism or a cooling mechanism to thereby control the temperature at which the ISOTC is adsorbed. When the adsorbing agent contained in the adsorbing device has adsorbed the ISOTC to a saturated level, the adsorbing agent can be recovered by passing a heating medium such as steam through it.

In accordance with the present invention, it can be noted that the introduction of the ISOTC into the air within the treating chamber may be carried out by spraying an ISOTC liquid or a solution thereof directly into the air and gasifying it In the air, in addition to the admixture of the gasified ISOTC with the air in the vapor-generating chamber. Further, it can be noted that the ISOTC can be removed from the air in a chemically reactive manner, not by the aid of the adsorbing agent, by using a substance having reactivity with the ISOTC, such as a solid amine or the like.

The treating chamber may be of any structure as long as it is of a closed structure. The gases containing the ISOTC may be introduced continuously into the treating chamber 3, unlike an intermittent introduction in the manner as described hereinabove, and discharged continuously therefrom through the line 14. In this case, a portion of the gases discharged from the line 14 may be recirculated into the treating chamber 3 through a flow valve.

The treatment of the material to be treated in the treating chamber 3 may be carried out in a continuous manner or in a batchwise manner. In treating the material to be treated in a continuous manner, the material may be conveyed through the treating chamber 3 at a constant speed.

The material may be made of fiber, molded plastic, and so on. The fiber may include various synthetic fibers, semi-synthetic fibers and natural fibers. Such may specifically include, for example, polyester fiber, nylon fiber, acrylonitrile-type fiber, cotton fiber, silk fiber, wool fiber, rayon fiber, polyolefin-type fiber and so on. Such fiber may be in a form of, for example, mono-filaments, multi-filament, short fibers, composite fibers, twisted yarn or the like. As the material made of the fiber, there may be employed a variety of material made or formed by using the aforesaid synthetic, semi-synthetic or natural fibers. And the material made of the fiber may be in a form of fabrics, knitted clothes, non-woven clothes and so on.

In accordance with the present invention, the fiber or the material made of the fiber so made or formed as to contain the ISOTC in the manner as described hereinabove is coated on its surface with a resin to thereby control the amount of the ISOTC to be evaporated or gasified from the surface of the fiber. In this case, the resin coating may be carried out by immersing, spraying or the like. The resin to be employed for the resin coating may be a conventional one and it may include, for example, a thermoplastic resin such as of an acrylic type, a vinyl type, a polyamide type and so on; and a thermoserring resin such as of an amino type, a phenol type, a polyester type, an epoxy type, an isothiocyanate ester type and so on. These resins may be coated in a form of a solution, an emulsion or the like.

The fiber and the material made of the fiber in accordance with the present invention can discharge the ISOTC vapor from its surface, so that it has both germicidal action and germistatic action. Hence, bags and bags in the form of a net, made of the fiber or the material made thereof, can advantageously be applied as a packaging material having antifungal activity as well as germicidal activity.

Plastic films may be employed as a material to be treated with the ISOTC vapor.

The plastic films may include a variety of films of a polyolefin type, a vinyl chloride type, a polyester type, an acrylonitrile type, and so on.

The plastic films obtainable by treating them with the ISOTC vapor so as to contain the ISOTC are then coated on their surfaces with a resin, thereby controlling an amount of the ISOTC to be evaporated from the film surfaces. The method for coating them with the resin may include, for example, immersion method, spraying method and so on. The resins to be used for coating them may include, for example, conventional ones, such as thermoplastic resins of an acryl type, a vinyl type, a polyamide type or the like, and thermoserring resins of an amino type, a phenol type, a polyester type, an epoxy type, an isocyanate or the like. These resins may be employed in the form of a solution or an emulsion in coating.

As a plastic container, there may be employed any one in which at least a portion of the material has an adsorbing property for the ISOTC vapor. As the material having the adsorbing property for the ISOTC vapor, there may be mentioned, for example, a variety of plastics of a polyolefin type, a vinyl chloride type, a polyester type, an acrylonitrile type, a vinyl acetate type, and so on. These plastics may be of a foamed body or of a semi-foamed body and such a foamed plastic may be preferred in terms of adsorption to the ISOTC vapor. Other materials capable of adsorbing the ISOTC vapor may include, for example, paper, corrugated cardboard, rubber, non-woven cloth, natural or synthetic fibers.

The container according to the present invention may be preferably of such a structure that its exterior surface is so coated or covered with a material incapable of substantially adsorbing the ISOTC vapor as to prevent or control evaporation of the ISOTC vapor from the exterior surface of the container. Such a material incapable of adsorbing the ISOTC vapor may include, for example, a metal or a synthetic resin, such as aluminium, stainless steel, nylon, polyvinylidene chloride or the like. In order to provide the container with its exterior surface coated or covered with such a material, the non-adsorbing material in the form of a sheet, film, plate or the like may be laminated on and adhere to a surface of the molded or formed material.

The container may be arbitrary in a shape or size and it may be of any shape such as in the form of a tray, box, bag, corrugated cardboard, pot or the like, with or without a lid.

The container according to the present invention may be employed for placing a variety of articles which may cause the problem involved with generation or formation of fungi or growth or proliferation of harmful microorganisms. Such articles which may be involved with the generation of fungi may include, for example, food including fresh food and processed food, such as vegetables, fish, fruits, ball bearings, precision machine parts such as packing materials, optical parts such as lenses, and so on. Industrial products such as paints containing natural polymers such as gelatin or the like may be mentioned, which may be transformed due to the growth or proliferation of microorganisms.

When the articles are packed with the container according to the present invention and conveyed, they may be protected from harmful action of microorganisms due to the germicidal or germistatic effects against the microorganisms adhering to the articles, resulting from the high germicidal action, including the germistatic action, resulting from the ISOTC evaporated from the container.

The container according to the present invention may advantageously be employed as a delivery box. When the delivery box with food placed or packed is delivered, the food placed within the box is protected from the harmful action of microorganisms or prevented from generation of fungi or transformation resulting therefrom, thereby retaining the high degree of freshness of food. After the delivery box may be collected, it may be cleaned and re-treated with the ISOTC vapor in the manner as described hereinabove, and re-used as a delivery box having the germicidal action and the effect of retaining a high degree of freshness of food.

(8) Germicidal Gas Composition, Process for the Preparation Thereof, and Apparatus Therefor In accordance with the present invention, there are further provided a process and an apparatus for the preparation of the germicidal gas compositions exhibiting the germicidal activity.

The processes and apparatuses may include:

(I) a process involving a step of bubbling gases into a liquid of the ISOTC or a mixed solution of the liquid of the ISOTC and an organic liquid (hereinafter referred to also merely as ISOTC-containing solution) and an apparatus for use in this process;

(II) a process involving a step of spraying the gases with the ISOTC-containing liquid and an apparatus for use in this process;

(III) a process involving a step of passing the gases through a column which is packed or filled with a porous material impregnated with the ISOTC-containing liquid and an apparatus for use in this process;

(IV) a process involving a step of bubbling the gases into the ISOTC-containing liquid and a step of passing the gases through a column which is packed or filled with a porous material impregnated with the ISOTC-containing liquid, and an apparatus for use in this process;

(V) a process involving a step of spraying the gases with the ISOTC-containing liquid and a step of passing the gases through a column which is packed or filled with a porous material impregnated with the ISOTC-containing liquid, and an apparatus for use in this process; and (VI) a process preparing the gases containing the ISOTC vapor in a given concentration by mixing a required amount of the gases with the gases containing the ISOTC vapor as prepared by the process (I) to (V), and an apparatus for use in this process.

Also, the present invention provides a packing method for packing food, which is characterized by filling a packing material for packing food with the gas composition prepared by each of the processes (I) to (VI).

Further, the present invention provides a novel gas composition having germicidal action, which comprises nitrogen gas or carbon dioxide gas containing the ISOTC vapor.

Figure 4:
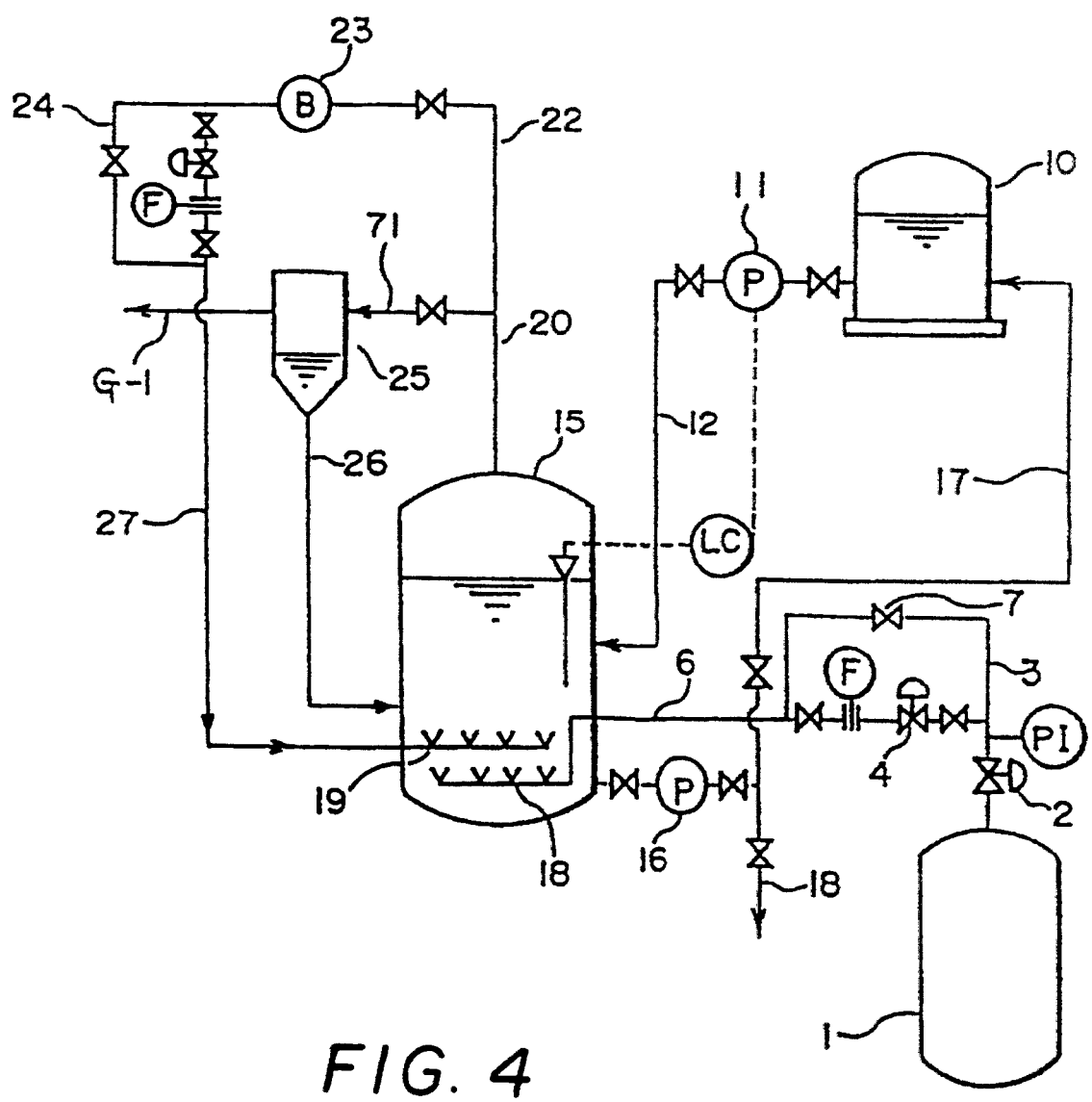
FIG. 4 is a flow sheet for a process for preparing germicidal gas composition containing the ISOTC.

FIG. 4 is a diagrammatic representation of the apparatus for carrying out the process (I) above. In FIG. 4, reference numeral 1 denotes a nitrogen bomb, reference numeral 10 denotes a tank for the ISOTC-containing liquid, reference numeral 15 denotes a bubbling tank, reference numeral 25 denotes a mist separator, reference symbol PI denotes a pressure gauge, reference symbol F denotes a flow meter, and reference symbol LC denotes a level controller.

In order to prepare the gases containing the ISOTC vapor with the apparatus as shown in FIG. 4, a liquid containing the ISOTC is supplied from the tank 10 to the bubbling tank 15 through a line 12 by a pump 11. The amount of the liquid to be supplied to the bubbling tank 15 is adjusted by the level controller LC.

Then, a flow controlling valve 2 is opened to supply a compressed gas to a gas dispenser 18 fitted within the bubbling tank 15 through a line 6 and bubbled into the liquid, followed by withdrawal from the bubbling tank 15 through a line 20. In the bubbling step, the ISOTC vapor is mixed with the gases withdrawn from the bubbling tank 15, and the gases containing the ISOTC vapor is fed to the mist separator 25 in which the mist accompanying the gases are separated. The gases separated with the mist separator 25 is then circulated through a line 26 to the bubbling tank 15, and the gases containing the ISOTC vapor from which the mist was separated are then discharged from the mist separator 25 through a line G-1.

In the apparatus as described hereinabove, as needed, a portion of the gases withdrawn from the bubbling tank 15 through the line 20 is bubbled into the liquid through a line 22, a blower 23 and a line 27 and by the aid of a gas dispenser 19 mounted to the bubbling tank. The concentration of the ISOTC vapor within product gases to be withdrawn from the line G-1 can be increased in accordance with this operation.

When the product gases are to be prepared in the manner as described hereinabove, the amount of the liquid within the bubbling tank is gradually decreased as the preparation of the product gases proceeds. However, the amount of the liquid decreased can automatically be supplied by the actuation of the pump 11 in response to a signal from the liquid level controller LC. If the nature of the liquid within the bubbling tank 15 oversteps the predetermined extent, the liquid in the bubbling tank 15 is returned via a pump 16 and a line 17 to the tank 10 where the nature of the liquid is adjusted again or the liquid therein is discharged out of the system through a line 18.

Figure 5:
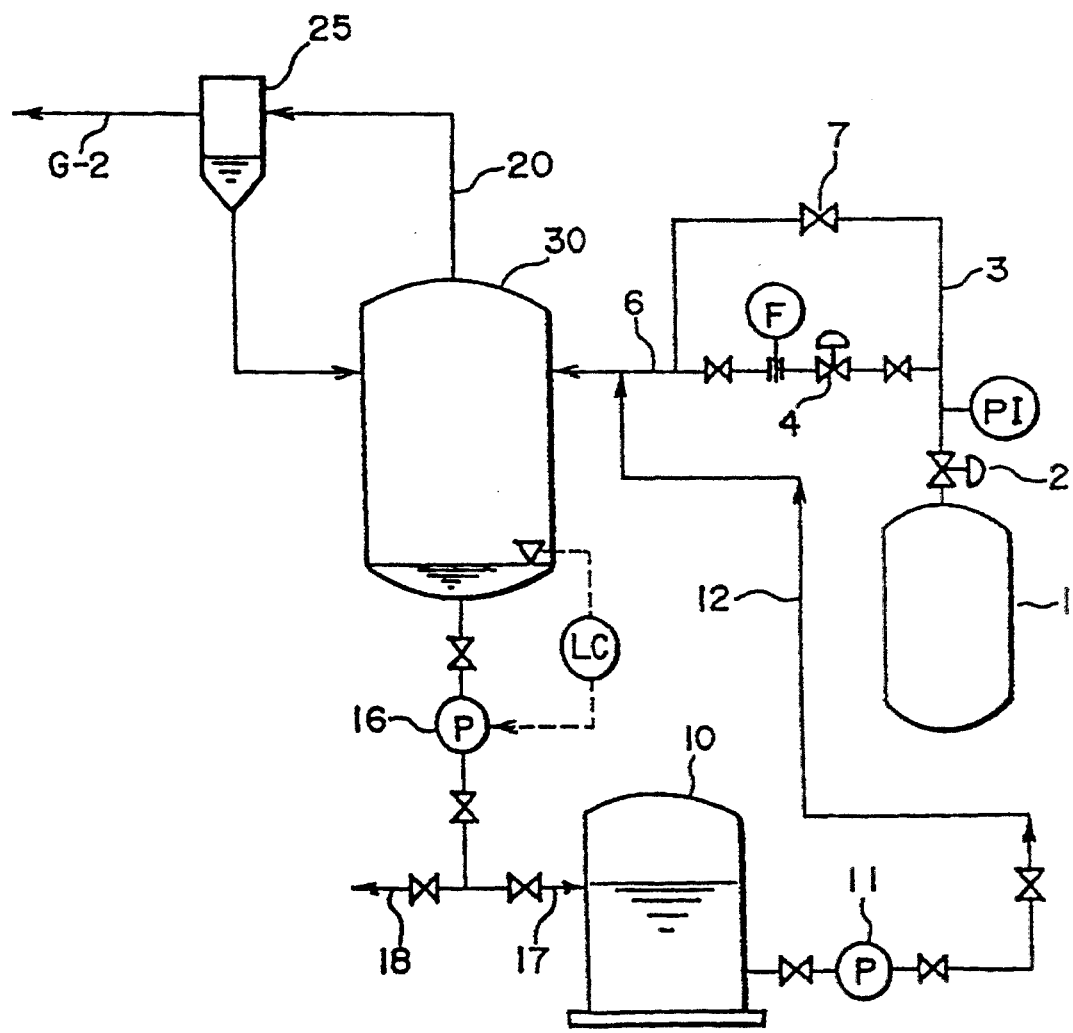
FIGS. 5 to 8 are flow sheets for variants of the processes.
Figure 6:
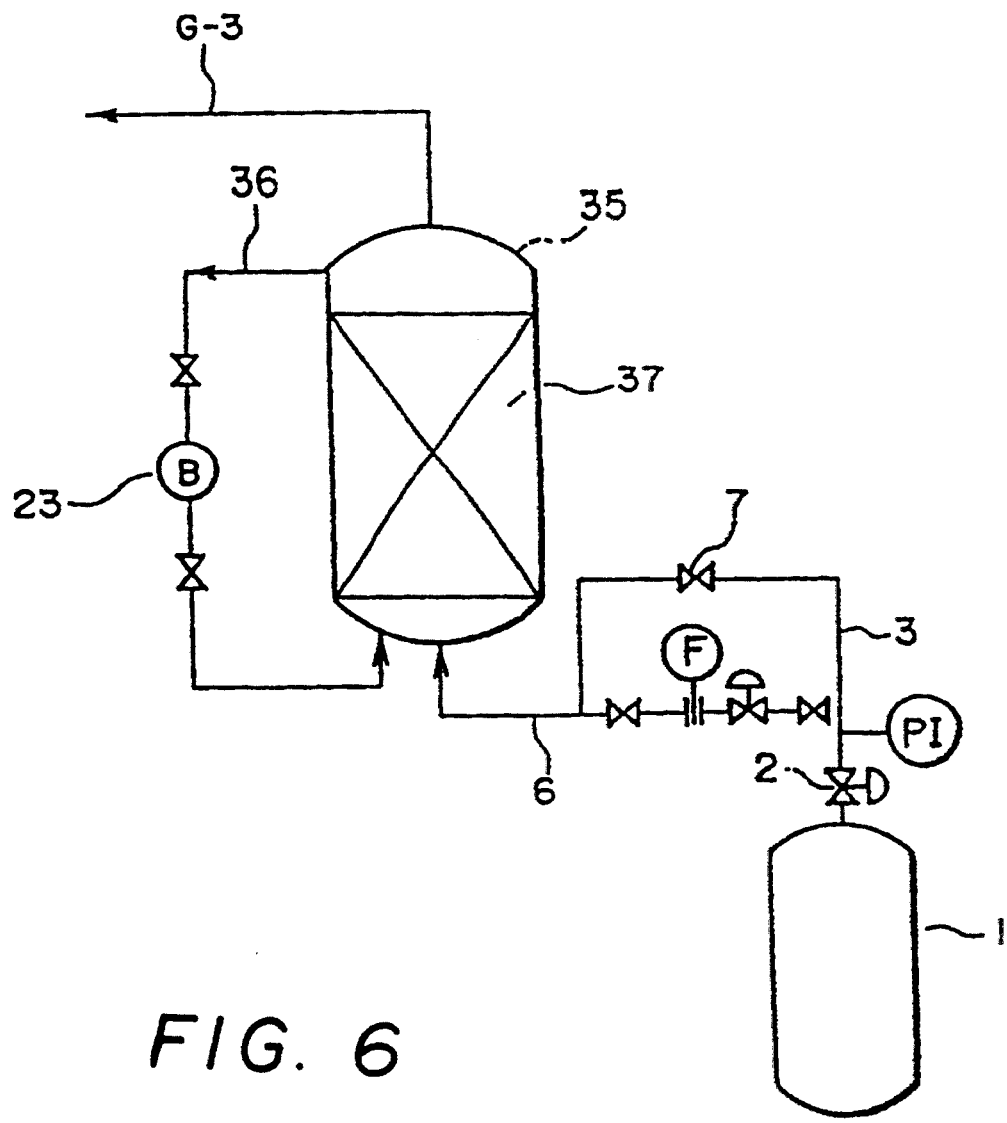
Figure 7:
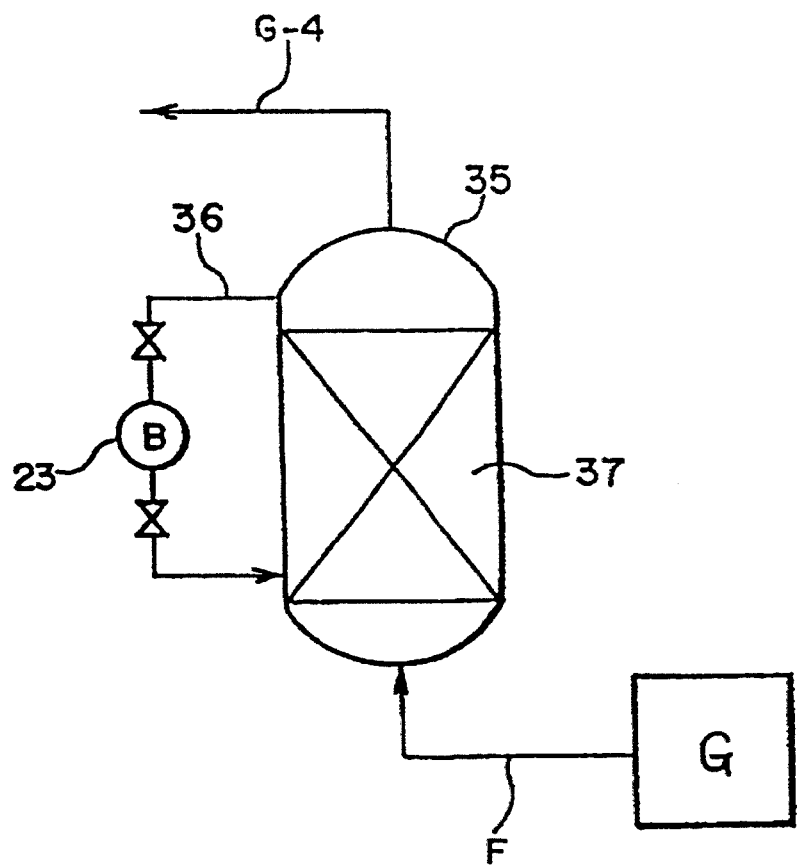
Figure 8:
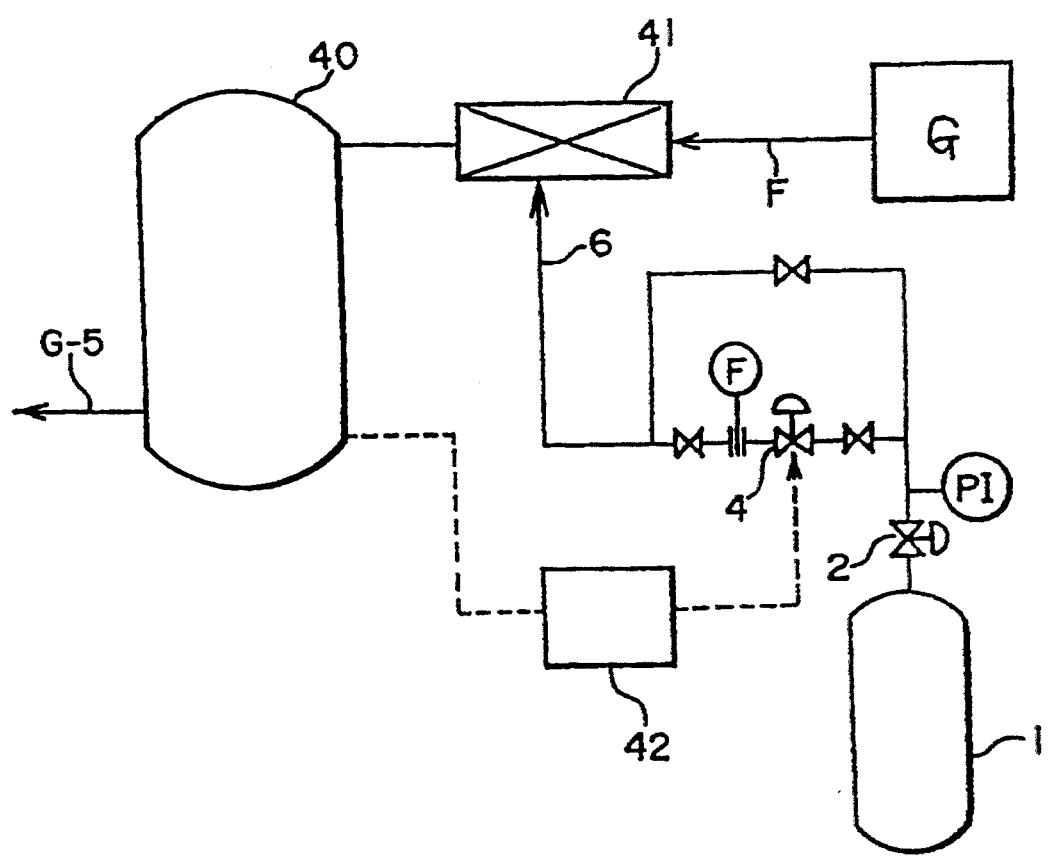

FIG. 5 is a diagrammatic representation of the apparatus for carrying out the process (II), in which reference numeral 30 denotes a spray tank and the other elements having the same functions are provided with the same reference numerals and symbols as in FIG. 4.

In order to prepare gases containing the ISOTC vapor with the apparatus as shown in FIG. 5, gases fed from a gas bomb 1 via the line 6 and the liquid containing the ISOTC discharged from the tank 10 via the line 12 are simultaneously sprayed through a two-liquid spray nozzle into a spray tank 30. And the gases containing the ISOTC vapor are discharged through the line 20 from the spray tank 30, followed by withdrawing product gases via the mist separator 25 through a line G-2. The condensed gases within the spray tank 30 are returned to the liquid tank 10 by the pump 16 through a line 17 or discharged outside the system through a line 18.

When the gases and the liquid containing the ISOTC are sprayed into the spray tank 30, it is also possible to introduce the gases into the spray tank 30 through a gas nozzle, not through the two-liquid spray nozzle as described hereinabove, while the liquid containing the ISOTC is sprayed into the spray tank 30 through a one-liquid spray nozzle, thereby mixing the gases with the liquid containing the ISOTC.

FIG. 6 is a diagrammatic representation of the apparatus for carrying out the process (III) as described hereinabove, in which reference numeral 35 denotes a column filled with a porous material 37 impregnated with the liquid containing the ISOTC, while the same and similar elements are provided with the same reference numerals and symbols as those shown in FIG. 4

As specific examples of the porous material, there may be mentioned, for example, active carbon, sepiolite, diatomaceous earth, silica, alumina, zeolite and so on. They may be of any shape or form, such as granules, cylinders, spheres, and so on.

In preparing the gases containing the ISOTC vapor by using the apparatus as shown in FIG. 6, the gases from the gas bomb 1 are first introduced into the column 35 through a line 6, thereby allowing the gases to pass through the column while being in contact with the porous material impregnated with the liquid containing the ISOTC, which in turn are packed within the column 35. The contact of the gases with the porous material allows the ISOTC impregnated within the porous material to be gasified as vapor which in turn is mixed with the gases. The resulting gases containing the ISOTC vapor is then withdrawn via a line G-3 from the column 35 as product gases.

When the product gases are prepared in the manner as described hereinabove, in cases where the length the porous material packed within the column 35 would be insufficient, where the speed of passing the gases through the column or where the concentration of the ISOTC vapor within the gases to be discharged from the line G-3 would be too low, it is preferred to circulate a portion of the gases withdrawn from the packed column to the column 35 through a line 36 via a circulating blower 23. The concentration of the ISOTC vapor within the product gases to be withdrawn through the line G-3 can be controlled by adjusting the amount of the gases to be circulated.

FIG. 7 is a diagrammatic representation of the apparatus for carrying out the process (III) or (IV). In FIG. 7, reference symbol G denotes an apparatus similar to the apparatus as shown in FIG. 4 or 5, respectively.

In preparing gases containing the ISOTC vapor by using the apparatus as shown in FIG. 7, product gases prepared by the apparatus G as shown in FIG. 4 or 5 are passed through a column 35 which has the structure similar to that shown in FIG. 6. The product gases are then withdrawn from the column 35 through a line G-4.

In this apparatus, mist of the ISOTC accompanying the gases within the column 35 can be removed, so that the mist separator 25 as used in FIGS. 4 and 5 can be omitted. Further, the column 35 is so arranged as to adjust the concentration of the ISOTC vapor Within the product gases passing through the line G-3 by operating a circulating blower 23 in the manner as described hereinabove. This serves as operating the apparatus G readily because the passage of the gases containing the ISOTC vapor through the column 35 can adjust the concentration of the ISOTC vapor within such a level as being practically applicable even if the concentration of the ISOTC vapor within the product gases prepared by the apparatus G would be too high or too low as compared with the applicable level.

FIG. 8 is a diagrammatic representation of the apparatus for carrying out the process (IV). In FIG. 8, reference numeral 40 denotes a buffer tank of a hollow container type, reference numeral 41 denotes a gas mixer, and reference numeral 42 denotes a control device containing a detection system for detecting the concentration of the ISOTC vapor such as a gas chromatography, etc. A system consisting of the buffer tank 40, the gas mixer 41, the control device 42 and a gas bomb 1 constitutes an apparatus for adjusting the concentration of the ISOTC vapor.

In order to provide product gases so adjusted as to contain the concentration of the ISOTC vapor by using the apparatus as shown in FIG. 8, the product gases prepared by the apparatus G as shown in each of FIGS. 4 to 7 are led to the gas mixer 41 through a line F while gases from the gas bomb 1 were supplied to the gas mixer 41, too, through a line 6. Both of the gases are then mixed within the gas mixer 41 and the resulting mixed gases are supplied to the buffer tank 40. The buffer tank 40 is connected to the control device 42 containing the detection system for the concentration of the ISOTC vapor, which transmits a detection signal to a flow adjusting valve 4, thereby allowing the detection signal to operate the flow adjusting valve 4 to feed the gases from the gas bomb 1 through the gas mixer 41 to the buffer tank 40 so as to adjust the concentration of the ISOTC vapor within the buffer tank 40. The product gases having the concentration of the ISOTC vapor adjusted to a predetermined level are then withdrawn from the line G-5.

The concentration of the ISOTC vapor within the product gases according to the present invention is adjusted to the range usually from 50 ppm to 1,000 ppm (v/v), preferably from 100 ppm to 500 ppm (v/v). As a carrier gas for the ISOTC vapor, there may be employed any gas capable of carrying the ISOTC vapor and such a gas may include, for example, nitrogen gas, carbon dioxide gas, air, and so on. When the product gases are to be employed for the purpose of germ-destroying food or retaining freshness of food, the use of nitrogen gas or carbon dioxide gas is advantageously for preventing transformation of food due to oxidation.

The gases containing the ISOTC vapor according to the present invention can be applied to various uses by taking advantage of the germ-destroying action of the ISOTC vapor.

In a preferred aspect of using the product gases according to the present invention, there is provided a process for packing food by filling a packing material with the product gases. In packing food with a plastic film or with a container, a packing material is filled with nitrogen gas or carbon dioxide gas, thereby Suppressing transformation of food due to oxidation or generation of mold or fungi from the food. As described hereinabove, the product gases according to the present invention are container as filling gases which can serve as effectively preventing from microbial transformation of food and as efficiently retaining or holding the high degree of freshness of food.

Further, the product gases according to the present invention can appropriately be employed for germicidally treating material or products which the growth of harmful microorganisms may cause problems. For instance, such harmful microorganisms adhering to those materials or products can be destroyed or killed by bringing them into the product gases containing the ISOTC vapor according to the present invention.

Furthermore, the product gases according to the present invention may be stored in a pressure-resistant container (compressire bomb) and they are practically applied to various uses for germ-destroying or sterilizing various products or articles by withdrawing them from the container.

It is also to be noted that the product gases according to the present invention can be employed for the preparation of materials or products having germicidal action. For instance, the germicidal materials or products may be prepared by placing fibers, containers such as boxes, paper, plastic films and so on in the product gases according to the present invention and allowing them to contain the ISOTC vapor contained within the product gases. The resulting germicidal materials or products are such capable of gradually evaporating or generating the ISOTC vapor therefrom and exhibiting germicidal or germ-destroying action.

The present invention will be described in more detail by way of examples.

EXAMPLE 1

As a sample, a fish (horse mackerel or saurel) which has been cut into halves, dried to a half-dry state and frozen, was defrozen and placed in a nylon bag in which 10 grams of silica gel (Sumikagel: Sumitomo Chemical Industries Co., Ltd.) packed in a small paper bag in turn was placed as a drying agent, and further 8 grams of granular diatomaceous earth impregnated with a 10% by weight allyl isothiocyanate (rate of impregnation:30% by weight) were placed therein as an agent for generating vapor of allyl isothiocyanate.

As a comparative purpose, the frozen horse mackerel cut into halves was defrozen and placed in a nylon bag in substantially the same manner as in the manner described immediately hereinabove, except for no use of allyl isothiocyanate as the agent for generating the allyl isothiocyanate vapor.

A packed body with the defrozen horse mackerel in a half-dry state was allowed to stand for five days and then opened. As a result, it was found that a decaying smell had generated from the sample for comparative purposes while no decaying smell had generated from the sample in accordance with the present invention. This means that the sample was subject to germ-destroying action by the allyl isothiocyanate vapor used for the present invention and has caused no decaying smell.

EXAMPLE 2

A pan was placed with 500 grams of polished rice and the rice was washed with water. Then, the rice was cooked in conventional manner after the addition of 0.5 cc of allyl isothiocyanate.

The cooked rice was packed with a plastic film and the bag was allowed to stand for four days. Then the bag was opened and, as a result of observation, it was found that the rice was subject to no transformation without any smell originating from allyl isothiocyanate.

As a comparative purpose, the rice was cooked in substantially the same manner as described immediately hereinabove. As a result of observation after a four-day storage, the cooked rice packed in a plastic film was found to generate strongly decaying smell.

EXAMPLE 3

In a nylon bag, there were placed 500 grams of polished rice and a paper bag with 15 grams of granular diatomaceous earth impregnated with soy bean oil having allyl isothiocyanate dissolved therein in the amount of 10% by weight (rate of impregnation: 30% by weight), and the nylon bag was closed. The nylon bag was opened after having been stored for one hour at room temperature, and the rice was washed with water and cooked in such conventional manner.

The cooked rice was packed with a plastic film and stored for four days in substantially the same manner as in Example 2. As a result, no change was seen in the cooked rice packed with the plastic film in the manner as described hereinabove.

EXAMPLE 4

(1) Preparation of Material for Retaining Freshness of Food

A filter paper (100 cm$^2$) was impregnated with 5 ml of a raw solution prepared by dissolving 1 part by weight of allyl isothiocyanate in 10 parts by weight of sesame oil, thereby yielding the material useful for retaining freshness of food. The odor generating from this material was that of sesame and the material did not substantially smell the odor of allyl isothiocyanate.

Separately, the material useful for retaining the degree of freshness of food was prepared by impregnating a filter paper (100 cm$^2$) with 5 ml of a raw solution prepared by dissolving 1 part by weight of allyl isothiocyanate in 10 parts by weight of olive oil. The odor generating from this material was that of olive and the material did not substantially smell the odor of allyl isothiocyanate.

(2) Tests for Retention of Freshness

A given amount of commercially available noodle was placed in a 1-liter container, together with the material for retaining freshness of food prepared in the manner as described hereinabove, and the packed food was allowed to stand in a closed state at room temperature. As a result, it was found that no fungi has occurred for a one-week storage and, when the container was opened, no odor originating from allyl isothiocyanate substantially smelled while fragrance of sesame or olive was imparted.

As comparison, a given amount of commercially available noodle was placed in a container at room temperature yet without containing any material useful for retaining freshness of food. In this case, it was found that fungi had occurred in four days.

EXAMPLE 5

As a test sample for a material to be fumigated, 500 grams of unmilled rice infected with rice wheevils was placed in a nylon bag in which a paper bag containing 5 grams of granular diatomaceous earth impregnated with soy bean oil so dissolved as to contain 10% by weight of allyl isothiocyanate (rate of impregnation: 30% by weight). Then the nylon bag was closed and allowed to stand for one day. After opening the bag, it was found that all of the rice wheevils were killed.

EXAMPLE 6

In a 5,000-ml container were twenty termites, and a flat glass dish with a lid so arranged as to have an opening, in which a mixture of 30% by weight of allyl isothiocyanate and 80% by weight of corn oil was so placed as to come into no contact with the termites.

As a result of observation, it was found that the motion of the termites became very slow in 10 minutes and the termites were killed in 2 hours.

EXAMPLE 7

Commercially available woven cloth made of polypropylene fiber was placed in a nylon bag. And diatomaceous earth impregnated with soybean oil dissolved in 10% by weight of allyl isothiocyanate (rate of impregnation: 30% by weight) was packed in a small paper bag and then the paper bag in turn was placed in the nylon bag, too. The nylon bag was then allowed to stand in a closed state for 30 minutes at room temperature and then opened to take the cloth out. After the cloth was allowed to stand for 24 hours, it was still found to smell like mustard and confirmed that the cloth has generated the allyl isothiocyanate vapor from its surface even after 24 hours.

EXAMPLE 8

Commercially available polypropylene film was placed in a nylon bag. And diatomaceous earth impregnated with soybean oil dissolved in 10% by weight of allyl isothiocyanate (rate of impregnation: 30% by weight) was packed in a small paper bag and then the paper bag in turn was placed in the nylon bag, too. The nylon bag was then allowed to stand in a closed state for 30 minutes at room temperature and then opened to take the film out. After the film was allowed to stand for 24 hours, it was still found to smell like mustard and confirmed that the film has generated the allyl isothiocyanate vapor from its surface even after 24 hours.

EXAMPLE 9

One of two 10-liter foamed styrol boxes was allowed to adsorb allyl isothiocyanate by filling the box with air containing 1,000 ppm (v/v) of allyl isothiocyanate.

Then, both of the two boxes were packed with five pieces of steamed bread and two rolls of bread and closed with a lid, followed by allowing them to stand at room temperature for predetermined period of time as follows. The results are shown as follows:

TABLE 1

| Days | Box of Present Invention | Box for Comparative Purpose |
| --- | --- | --- |
| 1 | No change of contents | No change of contents |
| 2 | No change of contents | Fungi generated on steamed bread |
| 3 | No change of contents | Malodor slightly occurred from steamed bread |
| 4 | No change of contents | Fungi generated on bread |
| 5 | No change of contents | Fungi generated even over the entire inside |

We claim:

1. A process for preparing a gas composition possessing germ-destroying action, said process comprising bubbling a gas into a mixture of a liquid isothiocyanic acid ester and an organic liquid having a boiling point of at least 180° C., said mixture containing 0.01–50% by weight of said liquid isothiocyanate acid ester, to obtain a gaseous admixture of said gas and a vapor of the isothiocyanic acid ester, said gaseous admixture containing 50 ppm to 1000 ppm v/v of said vapor.

2. A process according to claim 1, wherein said gas is at least one gas selected from the group consisting of nitrogen, air and carbon dioxide.

3. A process according to claim 1 further comprising diluting said gaseous admixture by adding an additional gas thereto to obtain said bacterial gas composition containing said vapor of isothiocyanic acid ester in a predetermined concentration.

4. A process according to claim 1 wherein said organic liquid has a vapor pressure at 30° C. of 2 mmHg or less.

5. A process according to claim 1 wherein said organic liquid has a vapor pressure at 30° C. of 1 mmHg or less.

6. A process according to claim 1 wherein said organic liquid has a boiling point of at least 220° C.

7. A process for preparing a gas composition possessing germ destroying action, said process comprising:
impregnating a column of a porous material impregnated with a mixture of a liquid isothiocyanic acid and an organic liquid having a boiling point of at least 180° C., said mixture containing 0.01–50% by weight of said liquid isothiocyanic acid; and
passing a gas through said column to obtain a gaseous admixture of said gas and a vapor of the isothiocyanic acid ester, said gaseous admixture containing 50 ppm to 1000 ppm v/v of said vapor.

8. A process according to claim 7, wherein said gas is at least one gas selected from the group consisting of nitrogen, air and carbon dioxide.

9. A process according to claim 7 further comprising diluting said gaseous admixture by adding an additional gas thereto to obtain said bacterial gas composition containing said vapor of isothiocyanic acid ester in a predetermined concentration.

10. A process according to claim 7 wherein said organic liquid has a vapor pressure at 30° C. of 2 mmHg or less.

11. A process according to claim 7 wherein said organic liquid has a vapor pressure at 30° C. of 1 mmHg or less.

12. A process according to claim 7 wherein said organic liquid has a boiling point of at least 220° C.

* * * * *

UNITED STATES PATENT AND TRADEMARK OFFICE
CERTIFICATE OF CORRECTION

PATENT NO. : 5,436,268
DATED : July 25, 1995
INVENTOR(S) : OHAMA et al

It is certified that error appears in the above-indentified patent and that said Letters Patent is hereby corrected as shown below:

Col. 1, line 37, "1" should read --1%--.
Col. 2, line 58, "gem" should read --germ--.
Col. 3, line 9, "gem" should read --germ--.
Col. 4, line 6, "gem" should read --germ--.
Col. 6, line 2, "bentonire" should read --bentonite--.
Col. 7, line 56, "gem" should read --germ--.
Col. 8, line 58, "gem" should read --germ--;
      line 60, "gem" should read --germ--.

Col. 16, line 5, after "line" insert --11--.
Col. 19, line 25, "In" should read --in--.
Col. 20, line 4, "thermoserring" should read
--thermosetting--; and
      line 30, "thermoser" should read --thermosetting--;
      line 31, delete "ring".
Col. 24, line 5, "Within" should read --within--; and

UNITED STATES PATENT AND TRADEMARK OFFICE
CERTIFICATE OF CORRECTION

PATENT NO. : 5,436,268
DATED : Jul. 25, 1995
INVENTOR(S) : Ohama et al

It is certified that error appears in the above-indentified patent and that said Letters Patent is hereby corrected as shown below:

Column 24, line 68, "Suppressing" should read —suppressing—.

Signed and Sealed this

Tenth Day of September, 1996

Attest:

BRUCE LEHMAN

Attesting Officer

Commissioner of Patents and Trademarks